(12) United States Patent
Aur (10) Patent No.: US 11,298,542 B2
(45) Date of Patent: Apr. 12, 2022

(54) METHOD AND SYSTEM FOR SUICIDE RISK ASSESSMENT AND INTERVENTION

(71) Applicant: Dorian Aur, London (CA)

(72) Inventor: Dorian Aur, London (CA)

(73) Assignee: AddBrain Inc, Vancouver (CA)

( * ) Notice: Subject to any disclaimer, the term of this patent is extended or adjusted under 35 U.S.C. 154(b) by 165 days.

(21) Appl. No.: 16/571,286

(22) Filed: Sep. 16, 2019

(65) Prior Publication Data

US 2021/0077814 A1 Mar. 18, 2021

(51) Int. Cl.

| | |
|---|---|
| *A61N 1/36* | (2006.01) |
| *A61B 5/00* | (2006.01) |
| *G16H 70/40* | (2018.01) |
| *G16H 50/30* | (2018.01) |
| *G16H 50/20* | (2018.01) |
| *A61B 6/00* | (2006.01) |
| *A61B 5/30* | (2021.01) |

(52) U.S. Cl.
CPC ........ *A61N 1/36096* (2013.01); *A61B 5/0006* (2013.01); *A61B 5/30* (2021.01); *A61B 6/501* (2013.01); *G16H 50/20* (2018.01); *G16H 50/30* (2018.01); *G16H 70/40* (2018.01)

(58) Field of Classification Search
CPC ...... A61N 1/36096; A61B 5/30; A61B 5/501; A61B 5/0006; G16H 50/30; G16H 50/20; G16H 700/40
See application file for complete search history.

(56) References Cited

U.S. PATENT DOCUMENTS

| | | | |
|---|---|---|---|
| 4,675,659 A | 6/1987 | Jenkins, Jr. | |
| 6,230,049 B1 | 8/2001 | Fischell | |
| 8,600,513 B2 | 12/2013 | Aur | |
| 9,691,411 B2 | 6/2017 | Scherer | |
| 2012/0150257 A1* | 6/2012 | Aur | A61N 1/36171 607/45 |
| 2012/0269906 A1* | 10/2012 | Sheehan | A61P 25/18 424/715 |

FOREIGN PATENT DOCUMENTS

WO WO-2020060111 A1 * 3/2020 ............ A61B 5/16

OTHER PUBLICATIONS

Iosifescu, D.V., et al, Pretreatment frontal EEG and changes in suicidal ideation during SSRI treatment in major depressive disorder . Acta Psychiatrica Scandinavica, 117: 271-276. https://doi.org/10.1111/j.1600-0447.2008.01156.x (Year: 2008).*

(Continued)

*Primary Examiner* — Brian T Gedeon
*Assistant Examiner* — Naveed R. Kolia (57) ABSTRACT

A brain mapping system and methods that allow to predict and monitor the risk of suicide and provide personalized therapy. The brain mapping system and methods detect if brain dysfunctions (injuries) are located in suicidal hubs that trigger increased suicidal ideation and high risk of suicide. The brain mapping technology is suited for different technologies and allows to monitor the effects of therapy, provide precise therapy to decrease the risk of suicide.

8 Claims, 6 Drawing Sheets

(56) References Cited

OTHER PUBLICATIONS

Aaltonen, K. I., Isometsä, E., Sund, R., & Pirkola, S. (2018). Decline in suicide mortality after psychiatric hospitalization for depression in Finland between 1991 and 2014. World Psychiatry, 17(1), 110-112.
Aur, D., Pang, C., Dipinto, A., Dobek, C., Blumberger, D., Downar, J., . . . & Vila-Rodriguez, F. (Sep. 2016). Resting State Delta Rhythms Change after rTMS in Treatment of Resistant Depression. In Journal of ECT (vol. 32, No. 3, pp. 216-216).
Aur, D., & Jog, M. S. (2010). Neuroelectrodynamics: understanding the brain language (vol. 74). IOS Press.
Aur, D., Jog, M., & Poznanski, R. R. (2011). Computing by physical interaction in neurons. Journal of integrative Neuroscience, 10(04), 413-422.
Aur, D., & Vila-Rodriguez, F. (2017). Dynamic Cross-Entropy. Journal of neuroscience methods, 275, 10-18.
Aur, D., & Jog, M. S. (2018). Focal and Diffuse Injuries on Dynamic Network Patterns are at the Origins of Major Depression, submitted.
Aur, D., Munjal V., Muller A., Virji-Babul N., (2018). Evidence of Brain Network Fragmentation 1-year Post Concussion in Adolescent Athletes: A Pilot Study, Poster session presented at the GF Strong Rehab Research Day.
Aur et al., 2019, Precise Application of Non-invasive Stimulation Removes Network Injuries in Treatment Resistant Depression, attached.
Aur, D., Toyoda, I., Bower, M. R., & Buckmaster, P. (2013). Seizure prediction and neurological disorder treatment. U.S. Pat. No. 8,600,513. Washington, DC: U.S. Patent and Trademark Office.
Aur et al., 2019, Suicidal Hubs in Major Depressive Disorders, attached.
Bates, D., Maehler, M., Bolker, B., & Walker, S. (2014). Fitting linear mixed-effects models using lme4. arXiv preprint arXiv:1406.5823.
Ballard, E. D., Luckenbaugh, D. A., Richards, E. M., Walls, T. L., Brutsché, N. E., Ameli, R., . . . & Zarate, C. A. (2015). Assessing measures of suicidal ideation in clinical trials with a rapid-acting antidepressant. Journal of psychiatric research, 68, 68-73.
Beck, A. T., Kovacs, M., & Weissman, A. (1979). Assessment of suicidal intention: the Scale for Suicide Ideation. Journal of consulting and clinical psychology, 47(2), 343.
Coito, A. L., Belo, D., Paiva, T., & Sanches, J. M. (2011). Topographic EEG brain mapping before, during and after Obstructive Sleep Apnea Episodes. In 2011 IEEE international symposium on biomedical imaging: from nano to macro (pp. 1860-1863). IEEE.
Hameroff, S., Trakas, M., Duffield, C., Annabi, E., Gerace, M. B., Boyle, P., . . . & Badal, J. J. (2013). Transcranial ultrasound (TUS) effects on mental states: a pilot study. Brain stimulation, 6(3), 409-415.
Hawton, K., Saunders, K. E., & O'Connor, R. C. (2012). Self-harm and suicide in adolescents. The Lancet, 379(9834), 2373-2382.
Kasten, F. H., Dowsett, J., & Herrmann, C. S. (2017). P202 Outlasting effect of transcranial alternating current stimulation (tACS) on individual alpha power decays within 90 min after stimulation. Clinical Neurophysiology, 128(3), e113.
Lenoir, C., Jankovski, A., & Mouraux, A. (2018). Anodal transcutaneous spinal direct current stimulation (tsDCS) selectively inhibits the synaptic efficacy of nociceptive transmission at spinal cord level. Neuroscience, 393, 150-163.
Mizuno, T., Takahashi, T., Cho, R. Y., Kikuchi, M., Murata, T., Takahashi, K., & Wada, Y. (2010). Assessment of EEG dynamical complexity in Alzheimer's disease using multiscale entropy. Clinical Neurophysiology, 121(9), 1438-1446.
Naeser, M. A., Martin, P. I., Ho, M. D., Krengel, M. H., Bogdanova, Y., Knight, J. A., . . . & Koo, B. B. (2016). Transcranial, red/near-infared light-emitting diode therapy to improve cognition in chronic traumatic brain injury. Photomedicine and laser surgery, 34(12), 610-626.
Narayana, S., Salinas, F., Boop, F., Wheless, J., & Papanicolaou, A. (2017). Transcranial magnetic stimulation. The Oxford Handbook of Functional Brain Imaging in Neuropsychology and Cognitive Neurosciences, 125.
Nock, M. K., Borges, G., Bromet, E. J., Cha, C. B., Kessler, R. C., & Lee, S. (2008). Suicide and suicidal behavior. Epidemiologic reviews, 30(1), 133-154.
Nock, M., Borges, G., & Ono, Y. (Eds.). (2012). Suicide: Global perspectives from the WHO world mental health surveys. Cambridge University Press.
O'Connor, R. C., & Kirtley, O. J. (2018). The integrated motivational-volitional model of suicidal behaviour. Phil. Trans. R. Soc. B, 373(1754), 20170268.
Olfson, M., Marcus, S. C., & Shaffer, D. (2006). Antidepressant drug therapy and suicide in severely depressed children and adults: A case-conlrol study. Archives of general psychiatry, 63(8), 865-872.
Oquendo, M. A., & Bernanke, J. A. (2017). Suicide risk assessment: tools and challenges. World Psychiatry, 16(1), 28.
Pinherio, J. C., and D. M. Bates, 1996, Unconstiained Parametrizations for Variance-Covariance Matrice. Statistics and Computing, vol. 6, pp. 289-296.
Palermo, G. B., & Ross, L. E. (1999). Mass murder, suicide, and moral development: Can we separate the adults from the juveniles?. International Journal of Offender Therapy and Comparative Criminology, 43(1), 8-20.
Simpson, G., & Tate, R. (2002). Suicidality after traumatic brain injury: demographic, injury and clinical correlates. Psychological medicine, 32(4), 687-697.
Stone, M., Laughren, T., Jones, M. L., Levenson, M., Holland, P. C., Hughes, A., . . . & Rochester, G. (2009). Risk of suicidality in clinical trials of antidepressants in adults: analysis of proprietary data submitted to US Food and Drug Administration. Bmj, 339, b2880.
Struve, F. A., Klein, D. F., & Saraf, K. R. (1972). Electroencephalographic correlates of suicide ideation and attempts. Archives of general psychiatry, 27(3), 363-365.
Teicher, Martin H., Carol A. Glod, and Jonathan O. Cole. Antidepressant drugs and the emergence of suicidal tendencies. Drug Safety 8, No. 3 (1993): 186-212.
Thibaut, A., Russo, C., Morales-Quezada, L., Hurtado-Puerto, A., Deitos, A., Freedman, S., . . . & Fregni, F. (2017). Neural signature of tDCS, tPCS and their combination: comparing the effects on neural plasticity. Neuroscience letters, 637, 207-214.
Vitanyi, P. M., & Li, M. (1997). An inkroduction to Kolmogorov complexity and its applications (vol. 34, No. 10). Heidelberg: Springer.
DaSilva, A. F., Volz, M. S., Bikson, M., & Fregni, F. (2011). Electrode positioning and montage in transcranial direct current stimulation. JoVE (Journal of Visualized Experiments), (51), e2744. https://www.jove.com/video/2744/electrode-positioning-montage-transcranial-direct-current.
Vitanyi, P. M. & Li, M. (1997). An introduction to Kolmogorov complexity and its applications (vol. 34, No. 10). Heidelberg: Springer, Receipt date: Sep. 16, 2019.

\* cited by examiner

METHOD AND SYSTEM FOR SUICIDE RISK ASSESSMENT AND INTERVENTION

CROSS-REFERENCE TO RELATED APPLICATIONS

This application claims priority from U.S. Provisional Patent Application 62/733,360 filed Sep. 19, 2018, which is incorporated herein by reference.

FIELD OF THE INVENTION

The present invention relates to the field of brain mapping. More specifically, the invention relates to predicting if a certain subject has suicidal ideation, increased risk to commit suicide, provide individualized, precise therapy and monitor the effects of therapy.

BACKGROUND OF THE INVENTION

Suicidal behavior is the leading cause of injury and death worldwide. Information about the epidemiology of such behavior is important for policy-making and prevention (Nock et al., 2008). The largest share of the intentional injury burden in developed countries is driven by suicide. In the United States, suicide is the 11th-leading cause of death it occurs among 10.8 per 100,000 persons, and accounts for 1.4 percent of all deaths (Nock et al., 2012). The understanding of the factors that contribute to suicide in people is a major challenge. About 80% of patients who die by suicide deny suicidal ideation when they are assessed by a mental healthcare professional (Busch et al., 2003).

In terms of suicide, major depression has the highest risk compared to other psychiatric disorders (Aaltonen et al., 2018). To quantify and assess suicidal intention Beck and coauthors have validated the Scale for Suicide Ideation (SSI) (see, Beck et al., 1979) a scale with 19 items that showed reliability and validity. Later analyses have shown that MADRS suicide items are sensitive to rapid changes in suicidal thoughts (Ballard et al., 2015; Simpson & Tate, 2002). The Montgomery Åsberg Depression Rating Scale (MADRS) can be used as a primary measure since MADRS suicide items have shown high correlations ($r > 0.80$) with the first five items of the Scale for Suicide Ideation SSI (SSI5).

About 60 percent of people that commit suicide are facing major depression, however the difference between suicidal depressed and just depressed individual is not easy to detect (Oquendo & Bernanke, 2017). Survivors affected by the violence of mass shootings always show signs of post-traumatic stress disorder and depression which may lead to suicide. Shooting survivors or those who lost a loved one are at greater risk of mental health issues (Palermo et al., 1999). In addition, it is likely that the same brain dysfunctions (network injuries) that lead to suicide can lead to deadly mass shootings, and mass violence.

Whole head quantitative electroencephalography (qEEG) can be used for multiple purposes to detect changes in brain health, monitor the effects of therapy or provide neurofeedback training systems. However, clinical application of topographic electroencephalography (EEG) mapping methods is still limited after almost 60 years of research even the progress in this field is remarkable (Coito et al., 2011; Fischell et la., 2001).

Importantly, our ability to predict suicide did not improve in the last 50 years (O'Connor et al., 2018). Despite proposed brain mapping methods (see, Struve et al., 1972) all previous techniques were unable to detect the presence of network dysfunctions that trigger suicidal ideation and none of known patents (e.g Scherer et al., 2017; U.S. Pat. Nos. 9,691,411; 4,675,659) is tailored to determine specific characteristics for individual patients related to suicidal risk. The method proposed in this patent overcomes the above issue and provide an objective measure beyond descriptive clinical scales.

SUMMARY OF THE INVENTION

The present disclosure describes an invention that has a number of embodiments that can be applied in combination with one another but may also have individual application. In one embodiment, there is provided a system and methods for brain mapping of a subject, the system comprising: a means for recording brain activity; a computing means, wherein the computing means is capable of identifying the location of network dysfunctions (injuries) in a group of patients that have increased risk of suicide based on psychiatric assessment and recorded electroencephalographic EEG activity. Network dysfunctions (injuries) are defined as the brain regions with abnormal network fragmentation. Network fragmentation can be estimated using nonlinear complexity measures and then mapped and displayed for specific brain regions. No reference to a control group is needed to compute or analyze normalized network fragmentation in single subjects. Linear regression models were used to determine the location of network injuries that have an increased risk to trigger suicidal behavior in groups of patients and determine suicidal hubs.

In another embodiment, the system and methods described herein are used to monitor the effect of therapy using network fragmentation maps (NFMs). Personalized therapy can include noninvasive, invasive stimulation or drug therapy. Brain mapping of network fragmentation makes easier to visualize and identify the location of network dysfunctions (injuries) associated with increased risk of suicide. The activity of the brain can be restored after drug administration or non-invasive stimulation or both of them combined. The foregoing general description and detailed description below are exemplary, but are not restrictive, of the invention.

BRIEF DESCRIPTION OF THE DRAWINGS

The accompanying drawings illustrate non-limiting examples of the present invention.

DETAILED DESCRIPTION OF THE INVENTION

Figure 1:
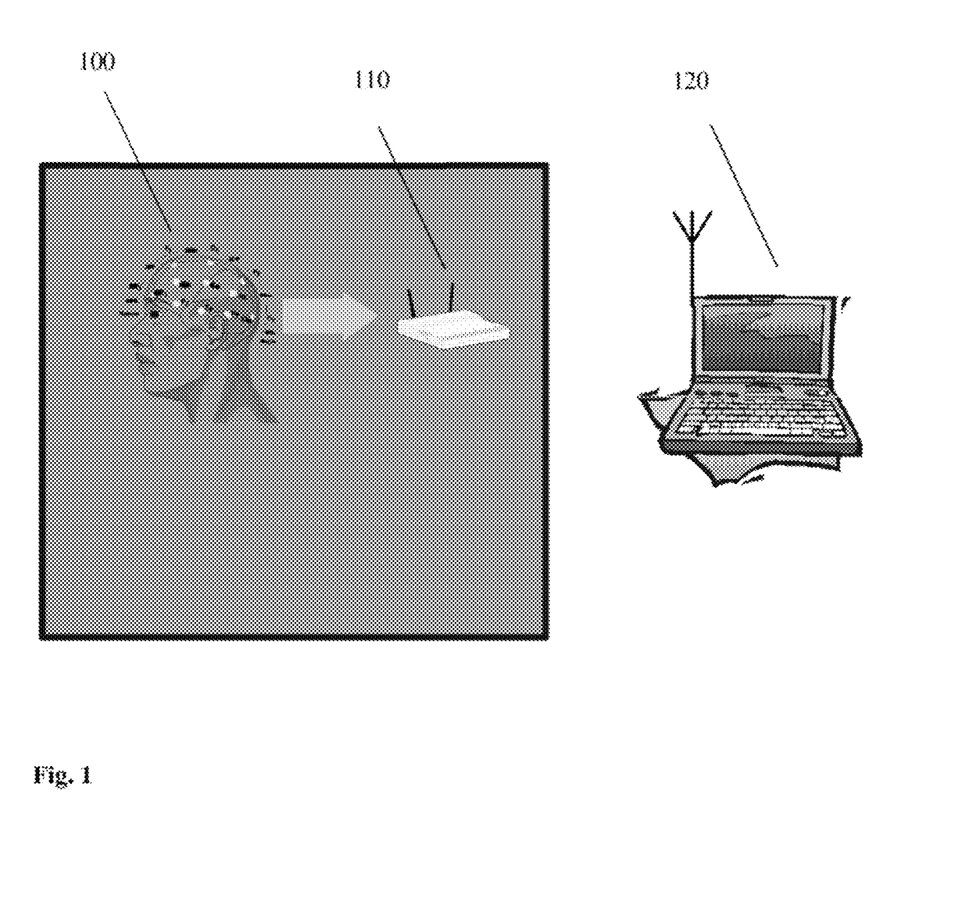
FIG. 1 is a schematic illustration showing a system of the present invention according to an example implementation. The system includes: an electroencephalograph (EEG) 110, a computing system 120 equipped with wireless transmission of information connected to a portable personal computer 130

The next description includes details and examples to provide an understanding of the patent. This invention is presented in different forms and not all unnecessarily details have been shown or described to avoid obscuring the invention. The drawings and specifications are explanatory, rather than restrictive. In FIG. 1 a schematic illustration a system of the present invention according to an example implementation. The system includes: an electroencephalograph (EEG) 110, a computing system 120 equipped with wireless transmission of information connected to a portable personal computer 130.

In one exemplary embodiment of the system brain maps that indicate regions with increased risk of suicide are built using recorded EEG data. Focal and diffuse injuries on dynamic network patterns were identified at baseline before drug therapy in patients with major depression using novel developed techniques. Network dysfunctions (injuries) are located in the brain regions with high, abnormal network fragmentation (Aur et al., 2018, Aur and Jog, 2019). The brain mapping procedure requires the subject to be connected to an encephalograph (EEG) that records electrical activity of the brain. The presence of network injuries in the regions labeled as "suicidal hubs" increases the risk of suicidal thoughts and suicidal behavior (Aur et al., 2019). The administration of antidepressants (escitalopram) and non-invasive stimulation can reduce network fragmentation in particular cortical, regions and has an impact on depression severity (Aur et al., 2019). In general, the administration of antidepressants reduces network fragmentation in the prefrontal cortical region, improves the mood and reduces suicidal thoughts. However, since each brain is different, in rare cases the administration of antidepressants may expand or shift the location of network dysfunctions (injuries) to "suicidal hubs" which will trigger increased suicidal ideation and the risk of suicide. These injured regions in patients with increased risk of suicide will generate differences in signature activation compared to control patients (Just et al., 2017).

Electrical interactions and inherent structural information from the dynamics between different parts of the brain are analyzed using various complexity measures and mapped. Network fragmentation is estimated based on the inverse of dynamic cross-entropy (DCE) values using resting state EEG data recordings. Dynamic Cross-Entropy (DCE) is defined as a multidimensional complexity measure that quantifies the degree of regularity of EEG signals in different frequency bands (see, Aur and Vila-Rodriguez, 2017). The resulting system will be less vulnerable to noise artifacts and volume conduction compared to previous techniques.

In an embodiment of the invention network dysfunctions (injuries) are the brain regions with high, abnormal increased network fragmentation. Normalized values of network fragmentation provide the regions with network injury that are brain mapped and used to monitor the effect of therapy or clinical worsening, the emergence of suicidal thoughts and behaviors. No reference to control group is needed to compute and display normalized network fragmentation maps (NFMs). In the examples provided herein, dynamic cross entropy is used without limiting the invention since other complexity measures could also be used to estimate network fragmentation of the brain network (e.g. Lyapunov exponent, algorithmic complexity measures such as Lempel-Ziv complexity, auto-mutual information, sample entropy, Tsallis entropy, approximate entropy, multiscale entropy (Vitanyi & Li, 1997; Mizuno et al. 2010). Also different clinician-administered questionnaire such Hamilton Depression Rating Scale (HAM-D), the Montgomery-Asberg Depression Rating Scale (MADRS) or Patient Health Questionnaire-9 (PHQ-9) can be used to assess the degree of depression severity. Continuous interactions between all brain regions are required for normal brain function (Aur et al, 2018; Aur et al., 2011; Aur and Jog, 2010, Aur and Tuszynski 2017). The brain maps of network fragmentation can be used to detect the location of network dysfunctions (injuries). In addition, linear mixed-effects models (Pinherio and Bates, 1996; Bates et al., 2014) are used to determine the relationship between the scalar variable represented by MADRS suicide items ($SSI_M$), and explanatory variables represented by network fragmentation estimated at baseline before therapy. The linear regression model can be written:

$$SSI_M = 1 + \Sigma_i a_i x_i + \Sigma_j b_j x_j + \varepsilon \text{ where } a_i > 0, b_j < 0 \quad (1)$$

If random effects can be neglected ($\varepsilon=0$), then suicide items $SSI_M$ can be approximated by two separated terms that depend on positive $a_i$, and negative coefficients $b_j$. The significance of the F-test indicates if the linear regression model provides a better fit to the data than the model that contains no explanatory variables. If the F-test indicates a good model fit, the brain regions with network fragmentation $x_i$ that correspond to high positive regression coefficients $a_i$ define the location of "suicidal hubs". An increase of suicidal ideation occurs once these brain regions become dysfunctional (injured). Contrarily, if the F-test indicates a good model fit, once injured the brain regions with network fragmentation $x_j$ and high negative $b_j$ coefficients will decrease suicidal ideation. The linear mixed-effects model was corrected for confounding factors such as age, sex. The presence of network dysfunctions (injuries) in two or more locations within suicidal hubs (high positive $a_i$ coefficients) has cumulative effect and increases the risk of suicide. The location of network dysfunctions in the brain regions with high negative $b_j$ coefficients will disrupt the presence of suicidal thoughts and diminish the risk of suicide.

Figure 2:
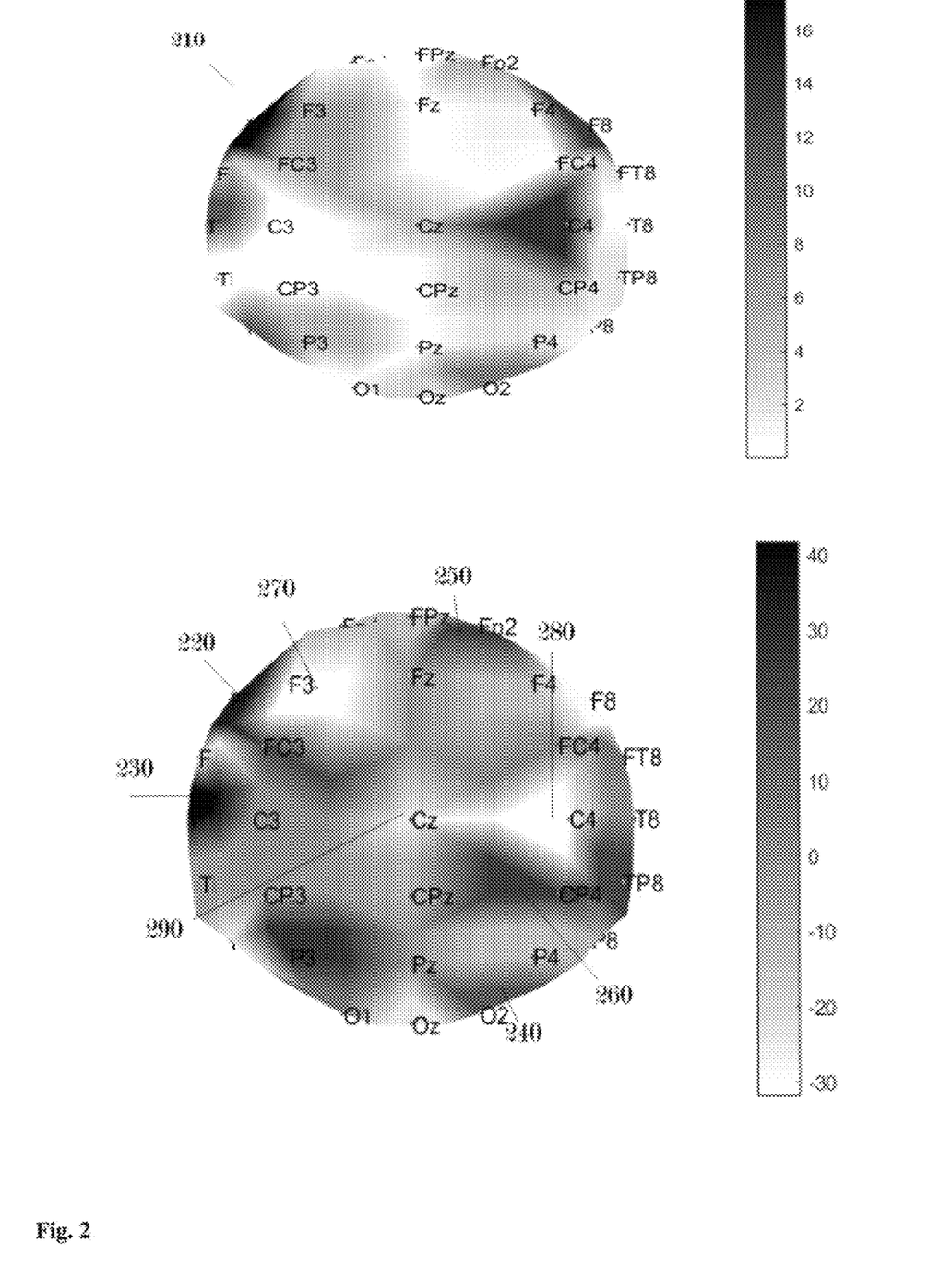
FIG. 2 displays a topographic map of F-test statistic for linear regression that in dark grey color 210 shows the location of network dysfunction (injuries) that are statistically significantly associated with signs of suicidal ideation. A high risk of suicide is associated with network dysfunctions (injuries) located in the brain regions with increased positive regression coefficients. Suicidal hubs are located in the brain regions associated with a statistically significant increase of suicidal ideation and high values of positive regression coefficients represented in dark gray color in the left frontal region at F7 site 220, left temporal cortex at electrode T7 230, right occipital region at O2 site 240, right frontopolar region at electrode at FP2 electrode, 250, right centroparietal region at electrode CP4, 260 and left sensorimotor cortex at electrode FC3. The risk of suicide is low if the network dysfunction (injury) is located in the regions with high negative regression coefficients represented in light grey color, at electrodes F3, 270, electrode C4, 280 and electrode Cz, 290.

The topographic map of F-test statistic for linear regression shows in FIG. 2 the location of network injuries in dark grey color that indicates a good model fit 210 and are statistically significantly associated with signs of suicidal ideation. Suicidal hubs are located in the brain regions associated with a statistically significant increase of suicidal ideation and high values of positive regression coefficients represented in dark gray color located in the left frontal region at F7 site, 220, left temporal cortex at electrode T7, 230, right occipital region at O2 site, 240, frontopolar region at electrode FP2, 250, or right centroparietal at electrode CP4, 260. The risk of suicide is low if the network dysfunction (injury) is located in the regions with high negative regression coefficients represented in light grey color, at electrodes F3, 270, electrode C4, 280 and electrode Cz, 290.

The presence of network injuries that expand to "suicidal hubs" located in the left frontal region at F7 site: $F(1,16)=17.48$, $p=0.0007$ that corresponds to Brodmann area 47 (BA47), left temporal region at site T7: $F(1,16)=11.5$, $p=0.003$ site that corresponds to BA42, right centroparietal region at electrode CP4: $F(1,16)=5.17$, $p=0.037$, right occipital region at site O2: $F(1,16)=8.8$, $p=0.008$ or right frontopolar region at site Fp2: $F(1,16)=5.49$, $p=0.03$ site and left sensorimotor cortex at electrode FC3: $F(1,16)=5.80$ $p=0.028$.

Figure 3:
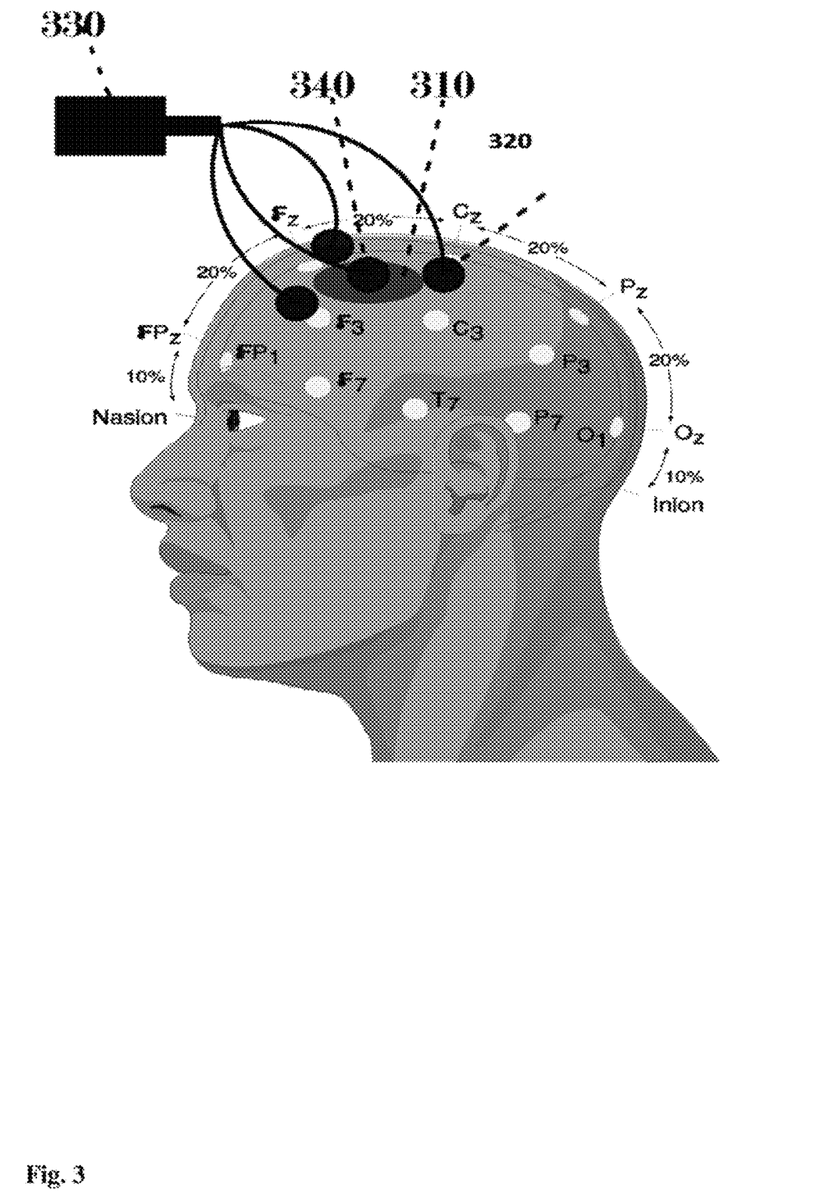
FIG. 3 displays a technique to locate and evaluate the extension of network injury 310 to determine the positioning of the built-on electrodes 320 to provide non-invasive stimulation. In order to maximize treatment benefit of non-invasive stimulation one electrode has to be located in the focal point of the network dysfunction (injury) 340. The generated current by the non-invasive system 330 will flow within the brain between the electrode located in the middle 340 and other electrodes 320. In general the other electrodes can have different locations which may include the right or left shoulder, right supraorbital ridge or spinal cord (see, Lenoir et al., 2018)

Accordingly, this invention overcomes the limitations presented above and provides a method to decrease the severity of depression and lower the risk of suicide. Once the location of network dysfunction (injury) is known, either non-invasive stimulation or various drugs can be used to provide therapy by targeting the detected brain region. The example presented in FIG. 3 shows how to shape the positioning of the built-on electrodes 320 to provide non-invasive stimulation by locating the extension of network dysfunction (injury) 310. In order to maximize treatment benefit of non-invasive stimulation one electrode is placed in the focal point where the network injury is located 340 and the other electrodes can encircle the network injury 310 or placed in distant regions, e.g. left shoulder or spinal cord. The generated current by the non-invasive system 330 will flow inside the brain between the electrode located in the middle 340 and other electrodes. It is recommended enough distance between the middle electrode and other electrodes to prevent increased current flow through the skin (DaSilva et al., 2011). The position of electrodes can have other locations that may include the right or left shoulder, right supraorbital ridge or spinal cord (see, Lenoir et al., 2018)

Other techniques such as transcranial alternating current stimulation (tACS) (Kasten et al., 2017) transcranial pulsed current stimulation (tPCS) (Thibaut et al., 2017) near-infrared light-emitting therapy (Naeser et al., 2016), transcranial ultrasound stimulation (Hameroff et al., 2013) or transcranial magnetic stimulation (Aur, et al., 2016; Narayana et al., 2017) can be used to target the network injury in order to remove increased network fragmentation or in specific cases to increase network fragmentation if the detected region shows very low network fragmentation levels. Drug therapy and non-invasive stimulation will alter molecular structure within neurons, synapses, glial cells and reshape dysfunctional networks. In addition, it was proved that repeated non-invasive stimulation changed electrical activity and removed network injuries (Aur et al., 2019). The system predicts and monitors the risk of suicide by mapping the location of network dysfunctions (injuries) using complexity measures in particular network fragmentation.

Figure 5:
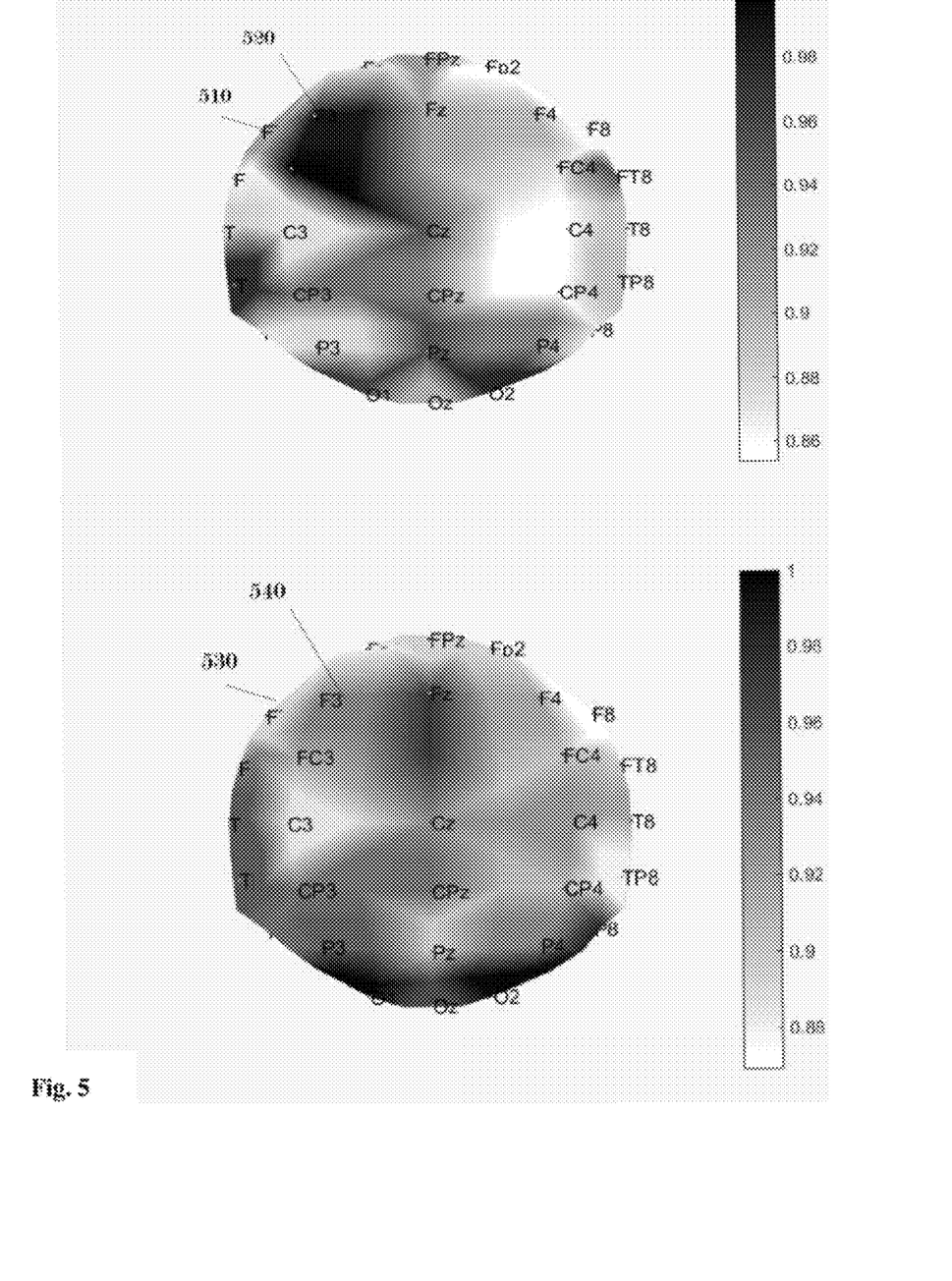
FIG. 5 displays a topographic brain map of normalized network fragmentation of a selected patient at baseline with mild depression and network injuries developed in the left dorsolateral prefrontal region (DLPFC) 510 and in the left frontal region at electrode F7, 520. Three months later after non-invasive stimulation the network injury cannot be detected in the left DLPFC 540 or at F7 site, 530. The depression symptoms and the risk of suicide are lifted.

In another embodiment the effect of noninvasive stimulation is revealed in FIG. 5. At baseline network dysfunctions can be observed in the left dorsolateral prefrontal region (DLPFC) 510 and in the left frontal region at electrode F7, 520 which is a suicidal hub. Three months later after non-invasive stimulation the network dysfunctions (injuries) located in the left DLPFC cannot be detected 540 or at F7 site, 530. The depression symptoms and the risk of suicide are lifted since network dysfunctions (injuries) are removed from the suicidal hub located at F7 site, 530.

Figure 6:
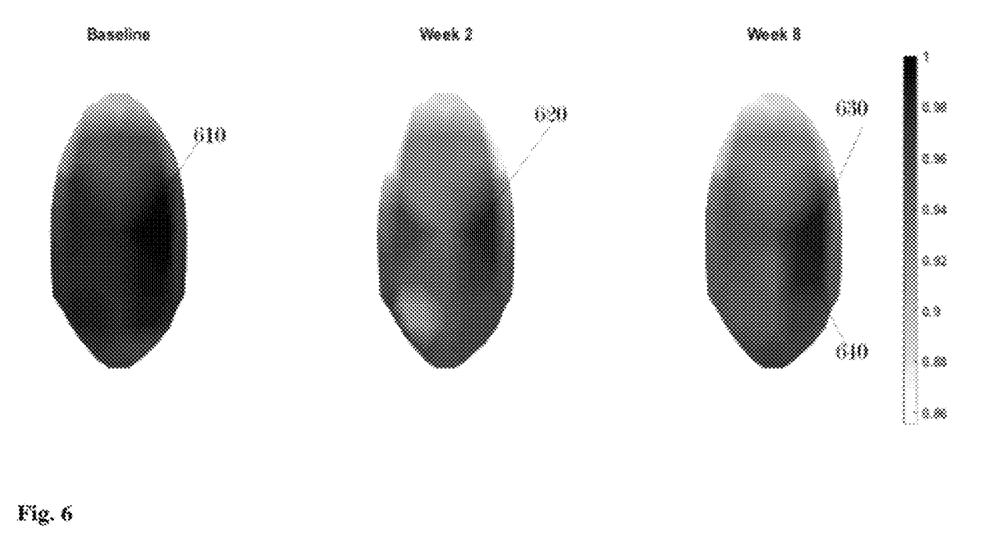
FIG. 6 displays the topographic plots of normalized network fragmentation of a selected non-remitter that shows network dysfunctions in dark gray color at baseline located in the right primary motor cortex at C4, 610 which is not a suicidal hub. This injury can be observed after two weeks of therapy 620. After over 8 weeks of escitalopram therapy the network injury expands from the primary motor region 630 to the right centroparietal region at CP4 site, 640 which is a suicidal hub and suicidal ideation $SSI_M$ increases from 1 to 2.

Normalized network fragmentation brain maps (NFMs) provide the regions with network dysfunctions (injuries) that can be used to monitor for clinical worsening and emergence of suicidal thoughts and behaviors (see, FIG. 6). Antidepressant therapy can shift the location of network injuries to different brain regions, see FIG. 6. At baseline, before therapy the initial location of network injuries is in the right primary motor cortex, see in dark color at C4, 610. This network dysfunction (injury) can be observed after two weeks of therapy 620. After over 8 weeks of escitalopram therapy the network injury expands from the primary motor region 630 to the right centroparietal region at CP4 site which is a suicidal hub, 640. As a result MADRS suicide, $SSI_M$ increases from 1 to 2.

Having shift the location of network dysfunction (injury) to the right centroparietal at electrode CP4 increases suicidal ideation and the risk of suicidal behavior since CP4 site is a suicidal hub (see FIG. 2, 240). This example shows that therapy can expand the network dysfunction (injury) toward suicidal hubs. Even though this phenomenon occurs in rare cases monitoring the effects of therapy in major depression is required since it can trigger an increased suicidal ideation and high suicidal risk especially in young people (Hawton et al., 2012). If drug therapy expands or shifts the location of network dysfunctions (injuries) to suicidal hubs suicidal thoughts and behaviors will emerge. The shift of network dysfunctions (injuries) to "suicidal hubs" explains previous FDA "black box warnings" for different psychostimulants and non-stimulant compounds such as atomoxetine or adderall (Strange, 2008). The risk of suicidal ideation or suicidal attempts doubles in youth treated with antidepressants compared to those treated with placebo (see, Brent, 2016). The presence of network dysfunctions (injuries) in two or more locations within suicidal hubs has cumulative effect and increases the risk of suicide.

EXAMPLES

Figure 4:
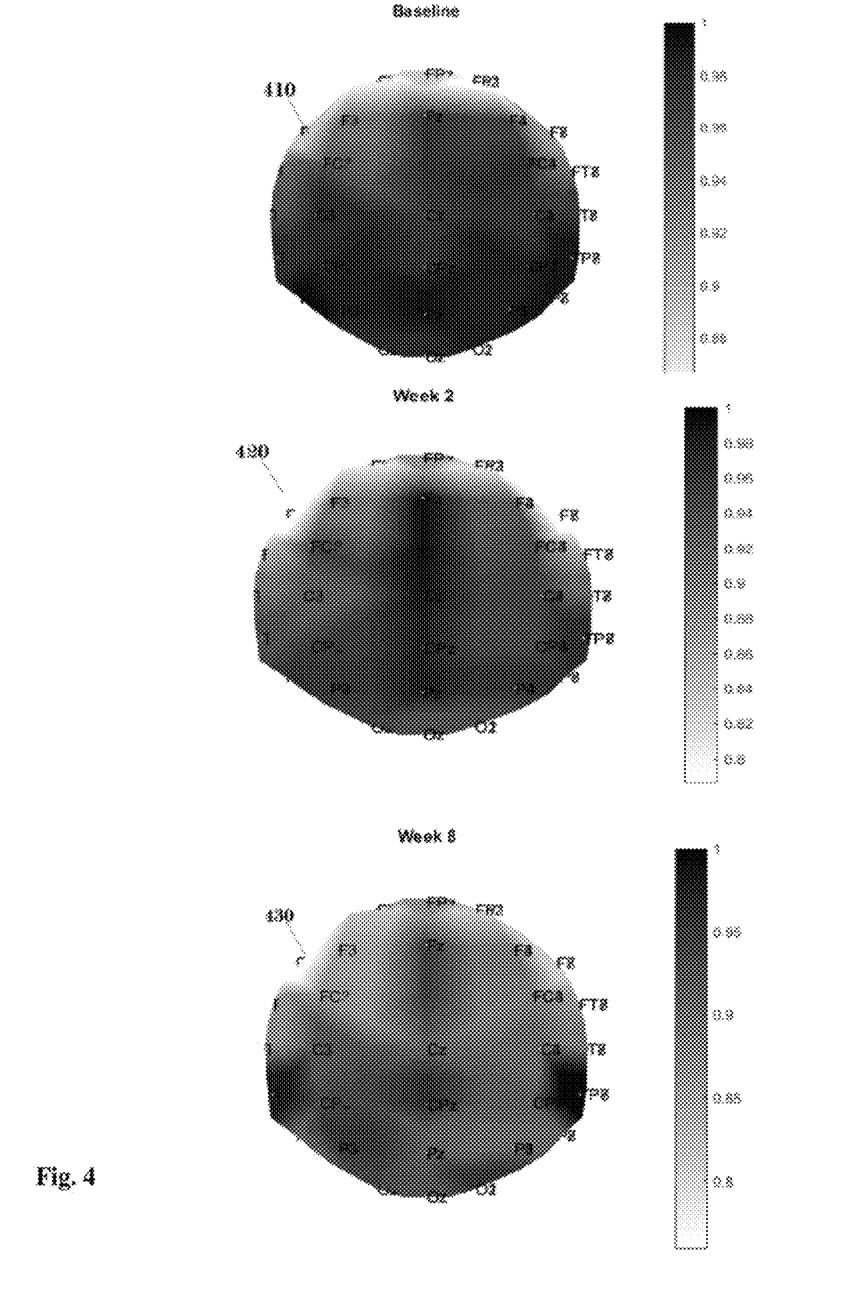
FIG. 4 displays a topographic map of normalized network fragmentation of a patient with major depression and network dysfunctions (injuries) located in "suicidal hubs". Two weeks after drug therapy the network dysfunctions (injuries) cannot be detected in the left frontal region or at F7 site 420. The severity of depression symptoms decreases from MADRS=27 at baseline to MADRS=3 after 8 weeks of escitalopram therapy. After 8 weeks of escitalopram therapy major depression symptoms and the risk of suicide is lifted, no network dysfunction (injury) can be observed at F7 site 430 or at CP4 site 440 which reduces suicidal ideation $SSI_M$ from 4 to 0.

Example 1: Topographic Network Fragmentation Map (NFM) is Used to Monitor the Effect of Drug Therapy The effect of therapy is monitored by displaying changes of network fragmentation that occur after the therapy to determine if network dysfunctions (injuries) are removed from or shifted to suicidal hubs. In FIG. 4 an example of a patient with network dysfunctions located in different suicidal hubs 410 that include the left frontal region at electrode F7, left sensorimotor cortex at electrode FC3, frontocentral brain region at electrode, FCz, right centroparietal region at CP4 site. Such network injuries are at origins of major depression and suicidal thoughts (Aur et al., 2019).

The severity of depression decreases from MADRS=37 at baseline to MADRS=29 at week2 of therapy and the network dysfunction (injury) cannot be detected in the left frontal region or at F7 site 420. After over 8 weeks of escitalopram therapy network fragmentation decreases globally and a reduction of depression severity is determined by the clinician the patient is in remission, the sign of depression are gone (MADRS=6). In addition the risk of suicide is lifted, no network dysfunctions injury can be observed in suicidal hubs at F7 site 430 or at CP4 site. The removal of network dysfunctions (injuries) from suicidal hubs substantially reduces suicidal ideation $SSI_M$ that drops from 4 to 0. No reference to control group was needed to estimate network fragmentation, or plot NFM in this case.

Example 2: Topographic of Normalized Network Fragmentation Map (NFM) is Used to Monitor the Effect of Non-Invasive Stimulation In one exemplary embodiment of the system and methods disclosed herein, noninvasive stimulation can be included in addition to drug therapy, see the example presented in FIG. 5 where a topographic representation of normalized network fragmentation is shown in a patient with mild depression at baseline. Network injuries can be observed in the left dorsolateral prefrontal region (DLPFC) 510 and in the left frontal region at electrode F7, 520. These network dysfunctions (injuries) are associated with major depression symptoms and their cortical location at F7 site inside a suicidal hub is a predictor of suicidal thoughts and suicide risk.

Three months later after non-invasive stimulation the injury cannot be detected in the left DLPFC 540 or at F7 site, 530. The depression symptoms and the risk of suicide are lifted since network dysfunctions (injuries) are removed from suicidal hub at F7 site.

Example 3: Topographic Representation of Normalized Network Fragmentation Map (NFM) Shows the Migration of Network Injuries to Suicidal Hubs During Drug Therapy In rare cases drug therapy can shift the location of network dysfunctions (injury) toward suicidal hubs and increase suicidal risk (Teicher et al., 1993; Olfson et al., 2006, Stone et al., 2009). This example show topographic plots of normalized network fragmentation of a selected non-remitter with the location of network dysfunctions in dark gray color at baseline. These network dysfunctions (injuries) are located in the right primary motor cortex at C4 electrode, 610. This injury can be observed after two weeks of therapy 620. The severity of depression also increases from MADRS=22 at baseline to MADRS=24 at week2 and remains at MADRS=22 after over 8 weeks of escitalopram therapy. After over 8 weeks of escitalopram therapy the network dysfunction (injury) expands from the primary motor region 630 to the right centroparietal region at CP4, 640. We already know that CP4 site is a suicidal hub and suicidal ideation $SSI_M$ increases from 1 to 2. This is the most interesting case since it shows that drug therapy can expand or shift network dysfunctions (injuries) to other brain regions. As a result of this spatial shift of network dysfunctions (injuries) other issues can potentially emerge and an increase of suicidal risk can be a side effect of therapy.

Therefore, if drug therapy affects brain networks, monitoring the effects of therapy is always required. In young people the administration of antidepressants can increase the severity of depression and shift the location of network dysfunction (injuries) to suicidal hubs.

REFERENCES

Aaltonen, K. I., Isometsä, E., Sund, R., & Pirkola, S. (2018). Decline in suicide mortality after psychiatric hospitalization for depression in Finland between 1991 and 2014. *World Psychiatry*, 17(1), 110-112.

Aur, D., Pang, C., Dipinto, A., Dobek, C., Blumberger, D., Downar, J., . . . & Vila-Rodriguez, F. (2016, September). Resting State Delta Rhythms Change after rTMS in Treatment of Resistant Depression. In *Journal of ECT* (Vol. 32, No. 3, pp. 216-216).

Aur, D, Tuszynski, J. A. (2017). A theory of structural evolution and interaction of matter, in Gordon, R., & Sharov, Habitability of the Universe before Earth: Astrobiology: Exploring Life on Earth and Beyond (series) (Vol. 1). Academic Press.

Aur, D., & Jog, M. S. (2010). Neuroelectrodynamics: understanding the brain language (Vol. 74). IOS Press.

Aur, D., Jog, M., & Poznanski, R. R. (2011). Computing by physical interaction in neurons. Journal of integrative Neuroscience, 10(04), 413-422.

Aur, D., Toyoda, I., Bower, M. R., & Buckmaster, P. (2013). U.S. Pat. No. 8,600,513. Washington, D.C.: U.S. Patent and Trademark Office Aur, D., & Vila-Rodriguez, F. (2017). Dynamic Cross-Entropy. Journal of neuroscience methods, 275, 10-18.

Aur et al., 2019, Focal and Diffuse Injuries on Dynamic Network Patterns are at the Origins of Major Depression, attached Aur et al., 2019, Precise Application of Non-invasive Stimulation Removes Network Injuries in Treatment Resistant Depression, attached Aur et al., 2019, Suicidal Hubs in Major Depressive Disorders, attached Bates, D., Machler, M., Bolker, B., & Walker, S. (2014). Fitting linear mixed-effects models using lme4. *arXiv preprint arXiv:* 1406.5823.

Ballard, E. D., Luckenbaugh, D. A., Richards, E. M., Walls, T. L., Brutsché, N. E., Ameli, R., . . . & Zarate, C. A. (2015). Assessing measures of suicidal ideation in clinical trials with a rapid-acting antidepressant. *Journal of psychiatric research*, 68, 68-73.

Beck, A. T., Kovacs, M., & Weissman, A. (1979). Assessment of suicidal intention: the Scale for Suicide Ideation. *Journal of consulting and clinical psychology*, 47(2), 343.

Busch K A, Fawcett J, Jacobs D G. Clinical correlates of inpatient suicide. J Clin Psychiatry. 2003; 64:14-19.

Coito, A. L., Belo, D., Paiva, T., & Sanches, J. M. (2011). Topographic EEG brain mapping before, during and after Obstructive Sleep Apnea Episodes. In 2011 *IEEE international symposium on biomedical imaging: from nano to macro* (pp. 1860-1863). IEEE.

DaSilva, A. F., Volz, M. S., Bikson, M., & Fregni, F. (2011). Electrode positioning and montage in transcranial direct current stimulation. *JoVE (Journal of Visualized Experiments)*, (51), e2744. https://www.jove.com/video/2744/electrode-positioning-montage-transcranial-direct-current Fischell, Robert E.; Fischell, David R. (Neuro Pace, Inc.) 2001 Integrated system for EEG monitoring and electrical stimulation with a multiplicity of electrodes, U.S. Pat. No. 6,230,049

Hameroff, S., Trakas, M., Duffield, C., Annabi, E., Gerace, M. B., Boyle, P., . . . & Badal, J. J. (2013). Transcranial ultrasound (TUS) effects on mental states: a pilot study. *Brain stimulation*, 6(3), 409-415.

Hawton, K., Saunders, K. E., & O'Connor, R. C. (2012). Self-harm and suicide in adolescents. *The Lancet*, 379 (9834), 2373-2382.

Jenkins Jr, Dale C., and Paul G. King. "Method and apparatus for signaling attempted suicide." U.S. Pat. No. 4,675,659. 23 Jun. 1987. 4675659

Kasten, F. H., Dowsett, J., & Herrmann, C. S. (2017). P202 Outlasting effect of transcranial alternating current stimulation (tACS) on individual alpha power decays within 90 min after stimulation. *Clinical Neurophysiology*, 128(3), e113.

Lenoir, C., Jankovski, A., & Mouraux, A. (2018). Anodal transcutaneous spinal direct current stimulation (tsDCS) selectively inhibits the synaptic efficacy of nociceptive transmission at spinal cord level. *Neuroscience*, 393, 150-163.

Mizuno, T., Takahashi, T., Cho, R. Y., Kikuchi, M., Murata, T., Takahashi, K., & Wada, Y. (2010). Assessment of EEG dynamical complexity in Alzheimer's disease using multiscale entropy. *Clinical Neurophysiology*, 121(9), 1438-1446.

Naeser, M. A., Martin, P. I., Ho, M. D., Krengel, M. H., Bogdanova, Y., Knight, J. A., . . . & Koo, B. B. (2016). Transcranial, red/near-infrared light-emitting diode therapy to improve cognition in chronic traumatic brain injury. *Photomedicine and laser surgery*, 34(12), 610-626.

Narayana, S., Salinas, F., Boop, F., Wheless, J., & Papanicolaou, A. (2017). Transcranial magnetic stimulation. *The Oxford Handbook of Functional Brain Imaging in Neuropsychology and Cognitive Neurosciences*, 125.

Nock, M. K., Borges, G., Bromet, E. J., Cha, C. B., Kessler, R. C., & Lee, S. (2008). Suicide and suicidal behavior. *Epidemiologic reviews*, 30(1), 133-154.

Nock, M., Borges, G., & Ono, Y. (Eds.). (2012). *Suicide: Global perspectives from the WHO world mental health surveys*. Cambridge University Press.

O'Connor, R. C., & Kirtley, O. J. (2018). The integrated motivational-volitional model of suicidal behaviour. *Phil. Trans. R. Soc. B*, 373(1754), 20170268.

Olfson, M., Marcus, S. C., & Shaffer, D. (2006). Antidepressant drug therapy and suicide in severely depressed children and adults: A case-control study. *Archives of general psychiatry*, 63(8), 865-872.

Oquendo, M. A., & Bernanke, J. A. (2017). Suicide risk assessment: tools and challenges. World Psychiatry, 16(1), 28.

Pinherio, J. C., and D. M. Bates, 1996, Unconstrained Parametrizations for Variance-Covariance Matrice. Statistics and Computing, Vol. 6, pp. 289-296.

Palermo, G. B., & Ross, L. E. (1999). Mass murder, suicide, and moral development: Can we separate the adults from the juveniles?. *International Journal of Offender Therapy and Comparative Criminology*, 43(1), 8-20.

Scherer, S., Pestian, J. P., & Morency, L. P. (2017). Speech or voice analysis techniques not restricted to a single one of groups specially adapted for particular use for comparison or discrimination for estimating an emotional state U.S. Pat. No. 9,691,411. Washington, D.C.: U.S. Patent and Trademark Office.

Simpson, G., & Tate, R. (2002). Suicidality after traumatic brain injury: demographic, injury and clinical correlates. *Psychological medicine*, 32(4), 687-697.

Stone, M., Laughren, T., Jones, M. L., Levenson, M., Holland, P. C., Hughes, A., . . . & Rochester, G. (2009). Risk of suicidality in clinical trials of antidepressants in adults: analysis of proprietary data submitted to US Food and Drug Administration. *Bmj*, 339, b2880.

Struve, F. A., Klein, D. F., & Saraf, K. R. (1972). Electroencephalographic correlates of suicide ideation and attempts. *Archives of general psychiatry*, 27(3), 363-365.

Teicher, Martin H., Carol A. Glod, and Jonathan O. Cole. (1993) Antidepressant drugs and the emergence of suicidal tendencies. *Drug Safety* 8, no. 3 186-212.

Thibaut, A., Russo, C., Morales-Quezada, L., Hurtado-Puerto, A., Deitos, A., Freedman, S., . . . & Fregni, F. (2017). Neural signature of tDCS, tPCS and their combination: comparing the effects on neural plasticity. *Neuroscience letters*, 637, 207-214.

Vitanyi, P. M., & Li, M. (1997). *An introduction to Kolmogorov complexity and its applications* (Vol. 34, No. 10). Heidelberg: Springer.

The invention claimed is:

1. A brain mapping method for predicting and monitoring the risk of suicide comprising:
   a. using electroencephalographic (EEG) signals and a computing system (device) to estimated network measures and topographically display a network fragmentation map of the whole brain to reveal a network dysfunction located inside a suicidal hub;
   b. detecting of proximity and finding when the position of said network dysfunction is in the proximity of said suicidal hubs which triggers suicidal ideation and increases the risk of suicide;
   c. predicting and monitoring of high risk of suicide when the network dysfunctions is located in the proximity or inside of said suicidal hubs that are further comprising the left frontal region at electrode F7 or left temporal region at T7 site or in the right occipital region at electrode O2 or frontocentral region at electrode FCz or fronto-polar regions at electrode FP2 or left sensorimotor cortex at electrode FC3 and right centroparietal region at CP4 site;
   d. providing a precise individualized therapy using a non-invasive or invasive stimulation or drugs to target the location of said network dysfunctions located in the proximity or inside of said suicidal hubs to diminish or remove the network dysfunction and reduce the risk of suicide.

2. The method as set forth in claim 1, determines the locations of the network dysfunctions using the network fragmentation map through visual inspection or automatically by the computing system detecting the color scale of said network fragmentation map.

3. The method as set forth in claim 1, that topographically maps estimated network complexity measures wherein said network fragmentation brain map is plotted as said by the computing system.

4. The method as set forth in claim 1, wherein said the presence of network dysfunctions (injuries)-in two or more locations within or in a proximity of said suicidal hubs has a cumulative effect and can increase or decrease the risk of suicide.

5. The method as set forth in claim 1, wherein said the removal of dysfunctional (injured) networks located within of said suicidal hubs or in their proximity by further therapy is required to reduce suicidal ideation and the risk of suicide and antisocial behavior.

6. The method as set forth in claim 1, wherein said non-invasive stimulation is set to target dysfunctional (injured) brain regions with as said network dysfunctions while the other electrodes can be placed far from dysfunctional regions located on shoulder or right supraorbital ridge or spinal cord.

7. The method and system as set forth in claim 1, predicts and monitors the effects of different therapies (drug administration) that could potentially trigger suicide or antisocial behavior by expanding or shifting the location of network dysfunctions (injuries) in the proximity of said suicidal hubs once therapy has started and after therapy.

8. The method as set forth in claim 1, further defines the proximity as less than minimum half distance between adjacent EEG electrodes of a 32 channel EEG system using 10-20 EEG placement.

* * * * *